Aug. 4, 1970 M. CROUX Plant Pat. 2,987
BUDDLEIA PLANT
Filed July 11, 1968
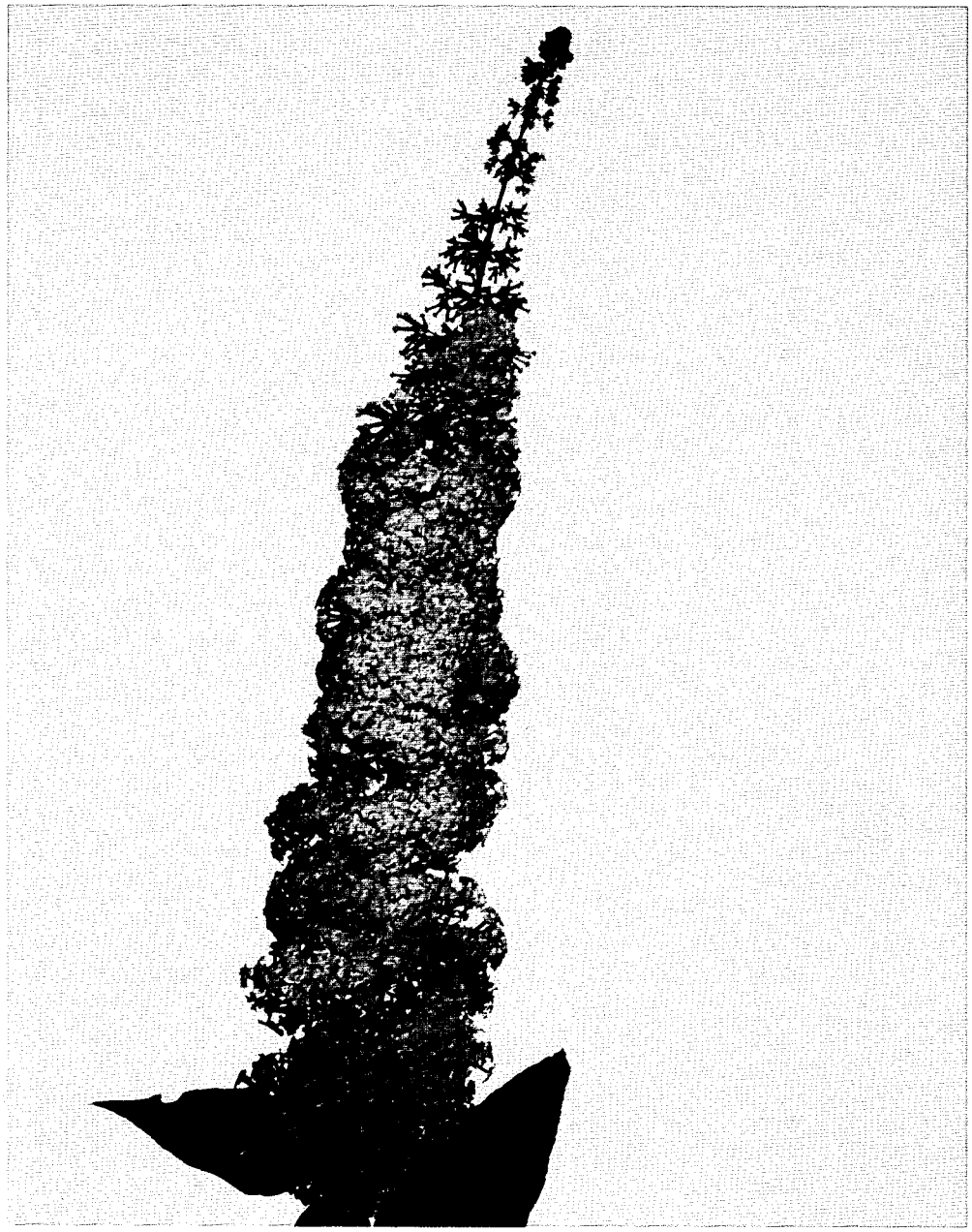
Inventor.
Maurice Croux
By: Robb & Robb
Attorneys.

United States Patent Office

Plant Pat. 2,987
Patented Aug. 4, 1970

2,987
BUDDLEIA PLANT

Maurice Croux, Hauts-de-Seine, France, assignor to Gulf Stream Products, Inc., Wachapreague, Va., a corporation of Virginia Filed July 11, 1968, Ser. No. 744,178
Int. Cl. A01h 5/00
U.S. Cl. Plt.—59 1 Claim The present invention relates to a new and distinct variety of Buddleia plant of the *magnifica* type of the species botanically known as *Buddleia davidi,* which was discovered in my nursery situated at Chatenay-Malabry, Hauts-de-Seine, France, as a newly found, cultivated seedling of unknown parentage.

At the time of the discovery aforementioned, I was growing in the fields of my nursery a block of seedlings of *Buddleia davidi magnifica.* My attention was attracted to one particular plant in this block which was about two feet tall and which bore flower spikes of exceptionally large size and of a distinctive and very attractive Peony Purple color, quite different in size and from the normal flower color of the flowers of all the others in the block, as well as different from those of any other Buddleia variety of which I am aware. I thereupon took steps to carefully preserve this new and unusual seedling and to asexually reproduce the same in my nursery, as performed under my direction and control by cuttings grown in my nursery at Chatenay-Malabry. Continued tests and observations of the original seedling and the progeny thereof, as produced from the cuttings aforesaid, fully convinced me that the new seedling was a new and improved variety having exceptionally good commercial value, as evidenced by the following unique combination of characteristics which distinguish the same from all other Buddleia varieties formerly known or available in commerce:

(1) A general resemblance in plant and flower form and habit to Buddleia varieties of the species botanically known as *Buddleia davidi magnifica*;

(2) Exceptionally large and showy floral spikes ranging as long as twenty-four inches or more; and (3) A distinctive and exceptionally attractive Peony Purple flower color.

The accompanying drawing shows a typical floral spike of my new Buddleia variety as depicted in color as nearly true as it is reasonably possible to make the same in a color illustration of this character.

The following is a brief description of the new Buddleia variety which generally conforms to that of the species botanically known as *Buddleia davidi magnifica,* except for its exceptionally large flower size and distinctive flower color, with color terminology in accordance with Robert F. Wilson's Horticultural Colour Chart, as based on observations made from specimens grown in France:

PLANT

Type: Shrub.
Class: *B. davidi magnifica.*
Parentage: A newly found seedling of unknown parentage.
Propagation: Holds its distinguishing characteristics through succeeding propagations by cutting.
Growth habit: Upright; from 3 feet to 4 feet tall.
Foliage: Lanceoleate; medium abundance.
*Upper surface.*—Smooth.
*Under surface.*—Rough.
*Ribs and veins.*—Prominent.
*Edge.*—Serrated.
*Color.*—New foilage: upper side—Nickel Green, Plate 57; under side—Pale Cypress Green, Plate 59. Old foliage: upper side—Parsley Green, Plate 00962; under side—slightly lighter than Parsley Green, Plate 00962.
Wood:
*New wood.*—Color—Nickel Green, Plate 57.
*Old wood.*—Color—Cypress Green, Plate 59.

FLOWERS

Blooming season: From July to frost.
Borne: In dense, terminal, erect or nodding panicles; normal form.
Size: Exceptionally large panicles ranging as long as 24 inches or longer.
Color: Peony Purple, Plate 729, with bright orange eye.
Reproductive organs: Normal.
Hardiness: Comparable to *B. davidi magnifica.*

I claim:

1. A new and distinct variety of Buddleia plant, substantially as herein shown and described, characterized particularly as to novelty by the unique combination of a general resemblance in plant and flower form and habit to those of the species botanically known as *Buddleia variabilis magnifica,* but being primarily distinguished therefrom by its exceptionally large and showy floral spikes ranging as long as twenty-four inches or more in length, and by its distinctive, exceptionally showy and attractive Peony Purple flower color.

No references cited.

ROBERT E. BAGWILL, Primary Examiner